United States Patent [19]

Mehler et al.

[11] Patent Number: 4,543,092
[45] Date of Patent: Sep. 24, 1985

[54] CATHETER SET

[76] Inventors: Doron Mehler, Warburghof 18, 3000 Hannover 61; Brigitte Otten, Im Schiffsmoor 41, 2850 Bremerhaven-Surheide, both of Fed. Rep. of Germany

[21] Appl. No.: 521,328

[22] Filed: Aug. 8, 1983

[30] Foreign Application Priority Data

Aug. 6, 1982 [DE] Fed. Rep. of Germany ... 8222222[U]

[51] Int. Cl.$^4$ .............................................. A61M 5/00
[52] U.S. Cl. .................................. 604/164; 604/239; 604/272
[58] Field of Search .............. 604/164, 170, 161, 168, 604/158–160, 239, 240, 272, 274, 188

[56] References Cited

U.S. PATENT DOCUMENTS 3,893,445  7/1975  Hofsess ................................ 604/239
4,239,042 12/1980  Asai .................................... 604/164
4,291,694  9/1981  Chai .............................. 604/162 X Primary Examiner—Stephen C. Pellegrino
Attorney, Agent, or Firm—Robert E. Burns; Emmanuel J. Lobato; Bruce L. Adams

[57] ABSTRACT

A catheter set comprises a syringe, a mandrin attachable to the syringe, a plastic canula that fits over the mandrin and a catheter attachable to a syringe and insertable through the canula when the mandrin is removed. The mandrin has a length of at least 50 mm and the tip of the mandrin is ground at an angle of at least 40° to the axis of the mandrin. Two facets are ground on opposite sides respectively of the mandrin tip. Small holes spaced in a lengthwise direction in the first 15 mm from the inner end of a catheter having an insertion length of 8 cm to 10 cm are circumferentially offset from one another.

6 Claims, 2 Drawing Figures

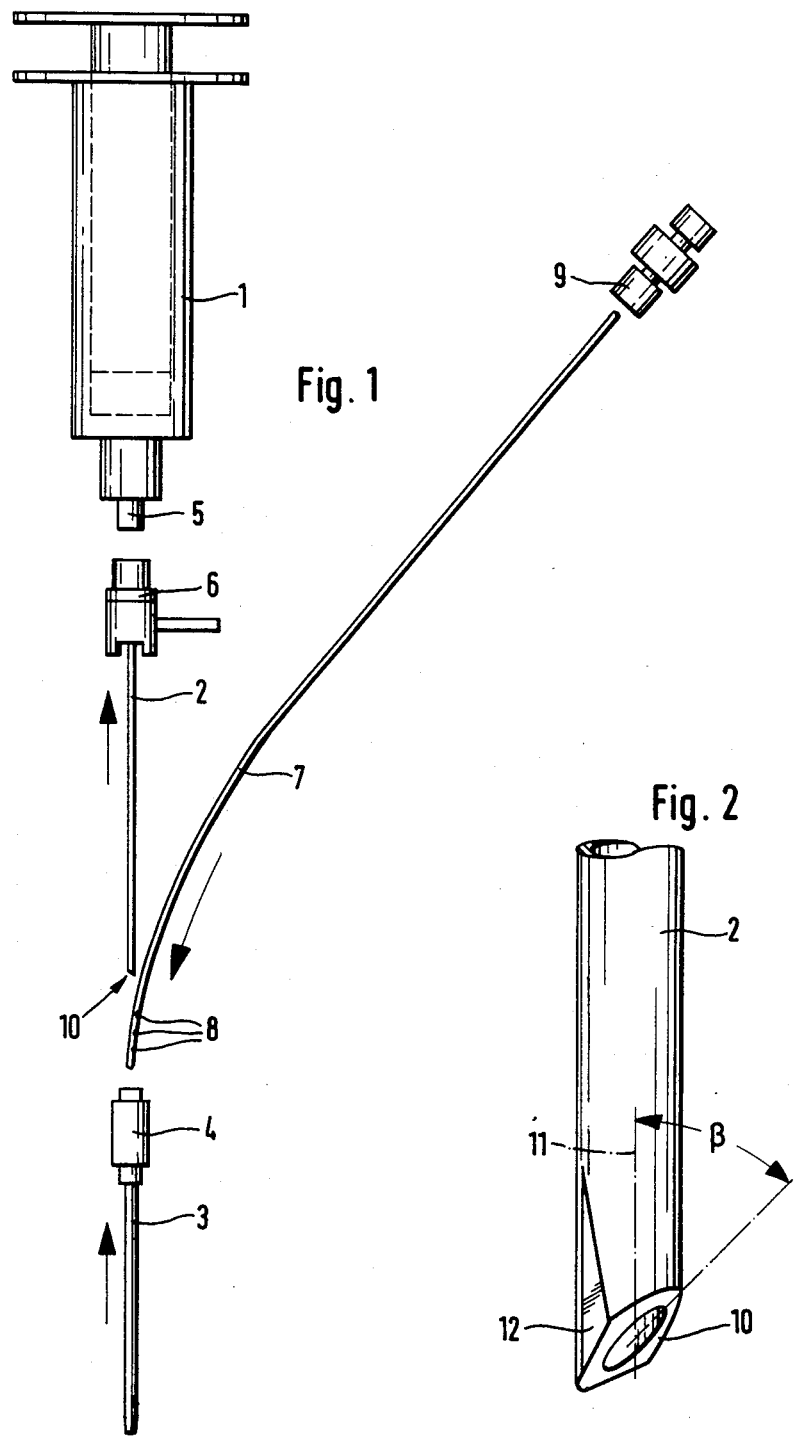

CATHETER SET

FIELD OF INVENTION

The invention comprises a catheter set comprising a syringe, a mandrin that can be connected to the syringe, a plastic canula which fits over the mandrin and is provided with a canula adapter and a flexible catheter which is insertable through the canula when the mandrin is removed and is provided with an adapter for attachment to the syringe, the outer diameter of the catheter being somewhat smaller than the inner diameter of the canula.

BACKGROUND OF INVENTION

Such catheter sets are used for a variety of purposes in a variety of fields of medicine but not for continuous plexus anathesia.

Since 1946, methods of continuous plexus anathesia with different modes of access to the plexus brachialis have been described. Heretofore to achieve this conductive anathesia only such adjuvants have been used as vein retention canulas, epideral catheters with Tuohy-needles, spinal needles with teflon catheters drawn over them, or also vein-puncturing canulas combined with vein retension catheters. An objection of all these methods is the danger of damaging the nerves and/or blood vessels through the sharp canula tip. Even the Tuohy-needle is not complete safe in these respects.

In order to avoid this danger of nerve and/or blood vessel damage through the sharp canula tip, an immobile needle of Zenz and Glocker has been developed for plexus anathesia (German Gebrauchsmuster No. 6810657.7). This needle makes possible the one time injection of a local anesthetic. When the effect of this has worn off, a new puncture must be made. The operation level reaches a maximum, the decline of which depends of the pharmacological properties of the local anesthetic to be used. By reason of its conception, this needle is suitable predominantly for analgesia or anesthesia of a maximum of six to ten hours and is hence used predominantly in the operative field. The shortness of the needle presents a relatively steep angle to the neurovascular axillary fasciae with the danger especially for beginners, of nerve lesion and possibly also blood vessel damage. The thin needle perforates neurovascular fasciae of the axilla with a light "click" phenomenon and a slightly evident decrease in resistance to a constantly exerted pressure through an attached syringe filled with a physiological NaCl-solution. With this needle, a catheter cannot be introduced into the nervovascular membrane.

SUMMARY OF THE INVENTION

It is an object of the invention to provide a catheter set for continous plexus anathesia with which even the inexperienced can introduce a catheter in the nervovascular membrane without nerve damage and assure a practically unlimited period of effect with the least possible traumatization.

In accordance with the invention the tip of the mandrin is ground at an angle of 35° to 45° and preferably more than 40° to the axial direction and the length of the mandrin is at least 50 mm.

Preferably the openings in the catheter introduced through the plastic canula are offset relative to one another and the openings are arranged in the first 15 mm of the catheter having an insertion depth of 8 to 10 cm.

Further, it is advantageous for the mandrin to be ground off on opposite sides of the extreme point of its tip.

In accordance with the invention the following advantages are attained:

1. By reason of the relatively flat angle of the canula to the neurovascular fasciae and the blunt angle at which the tip of the mandrin is ground, a relatively high force is required to perforate the fasciae. Similarly in periduralanathesia the lost of resistance is clearly perceptable and a "click" phenomenon is often clearly audible. In comparison to the use of a short needle, both phenomenon are quite marked.

On account of the flat puncture angle with the special canula tip, a nerve or blood vessel lesion is unlikely as the mandrin of the canula after perforation of the fasciae extends almost tangential to the blood vessels running inside the fasciae. Moreover, after perforation of the fasciae, the soft Teflon part of the canula is shoved over the mandrin into the nervovascular space. Also, in this, the danger of nerve or blood vessel lesion is avoided.

2. The administration of a parathesia is by observation of this procedure not necessary. As will be recognized, this is especially suitable for patients with whom communication is not possible (for example anethesia of extremely intoxicated patients, sympathicolis of intensive patients etc.). Through the rapid injection of a cold physiological NaCl-solution a traumatic parasthesia can often be relieved.

3. Through the decreased danger of blood vessel damage with hamatum formation and through the longer subcutaneous extent of the catheter to the perivascular space the possibility of an infection or of its spreading in the regio axillaris can be greater reduced by suitable care (daily bandage change, polyvidone iodine salve). In an average length of treatment of 14 to 21 days, no catheter removal was required by reason of infection. The longest time a catheter remained in place was seven weeks. Even here there was no infection.

4. For the beginner in anethesia there are the advantages of avoiding an intraneural injection, to be able to abandon the release from parathesia and with very much greater probability also analgize or anathesize the N. musculocutaneous.

BRIEF DESCRIPTION OF DRAWINGS

The essence of the invention will be further explained with reference to the accompanying drawings which show schematically a catheter set in accordance with the invention. In the drawings:

FIG. 1 is a schematic disassembled view of a catheter set in accordance with the invention; and FIG. 2 is an enlarged perspective view of the tip of the mandrin.

DESCRIPTION OF PREFERRED EMBODIMENT

A catheter set in accordance with the present invention comprises a mandrin 2 attachable to a syringe 1 and a plastic canula 3 which fits over the mandrin. The syringe comprises a cylinder 1a having a nozzle 5 and a plunger 1b operable by finger grips 1c and 1d provided respectively on the plunger and cylinder.

The mandrin 2 is in the form of a thin, hollow metal needle having a length of at least 50 mm. At its upper end the mandrin is provided with a plastic socket 6 which fits on the nozzle 5 of the syringe 1 with a pressure fit, the nozzle 5 being slightly tapered for this purpose. A finger piece 6a is provided on the socket 6 for convenient manipulation of the mandrin.

The canula 3 is a thin, plastic tube formed for example of nylon or teflon which fits snugly over the mandrin. At its upper end, the canula 3 has a plastic adapter 5 which has a substantially greater diameter than the canula and is provided with projections which fit in opposed recesses 6b provided in the lower end of the socket 6 of the mandrin to fix the canula non-rotatably on the mandrin. The canula 3 is of such length that when it is on the mandrin with the projections of the adapter 4 in the recesses 6b of the socket 6 of the mandrin the lower end of the canula is just short of the tip of the mandrin. Moreover, the lower end of the canula is slightly tapered so that the canula can easily enter a passage made by the mandrin.

A catheter 7 is insertable through the canula 3 when the mandrin 2 has been removed. The catheter 7 is a thin plastic tube having at its outer end an adapter 9 having a socket 9a for coupling the catheter to a syringe. The socket 9a is closed by a removable cap 9b. The catheter has a length of at least 8 to 10 cm. The inner end of the catheter is closed. In the first 15 mm from the inner end of the catheter there are provided a plurality of small openings 8 which are axially spaced and circumferentially offset relative to one another. The catheter has an outer diameter smaller than the inner diameter of the canula so that the catheter can pass freely through the canula.

Very important is the angle $\beta$ at which the tip of the mandrin 2 is sharpened. This angle $\beta$ between the end face of the tip and the axis 11 of the mandrin is between 35° and 45° and is preferably at least 40°. Moreover, side fascets 12 are advantageously ground on opposite sides of tip of the mandrin so that here the wall thickness of the mandrin is reduced. As seen in FIG. 2 the fascets 12 are tapered and blend into the wall of the mandrin. These fascets make easier the entry of the mandrin without the danger of damaging nerves. As seen in FIG. 2, the fascets 12 are symmetrical to one another relative to the plane of symmetry of the inclined end face of the tip of the mandrin.

What we claim is:

1. A catheter set comprising a syringe having an outlet, a hollow mandrin attachable to the syringe, means for removably connecting said mandrin to the outlet of said syringe, a plastic canula fitting closely over said mandrin, an elongate catheter insertable through said canula when said mandrin is removed from said canula, said catheter having an outside diameter somewhat less than the inside diameter of said canula and means for removably connecting an end of said catheter to the outlet of a syringe, said mandrin having a length of at least 50 mm and the tip of said mandrin being ground to form an end face disposed at an angle of approximately 35° to 45° to the axis of said mandrin.

2. A catheter set according to claim 1, in which the tip of said mandrin is ground to form an end face disposed at an angle of at least 40° to the axis of said mandrin.

3. A catheter set according to claim 1, in which said mandrin has tapered facets ground on opposite sides of the outermost part of its tip portion, said facets being symmetrical to one another with respect to an axial plane perpendicular to the end face of said mandrin and reducing the area of said end face without intersecting the bore of the mandrin.

4. A method of effecting continuous plexus anathesia which comprises connecting to the outlet of a syringe a mandrin with a plastic canula fitting closely over said mandrin, pressing said mandrin and cannula through the skin and flesh and a blood vessel wall of a patient into said blood vessel, removing the mandrin from said canula, inserting a catheter through said canula into said vessel and coupling the catheter to a syringe, thereby characterized that said mandrin has a length of at least 50 mm and blunt tip with an end face ground at an angle of approximately 35° to 45° to the axis of said mandrin, and that said mandrin with said canula thereon is inserted almost tangentially to said blood vessel, said blunt tip pushing nerves out of its path and signalling penetration of the blood vessel wall by a marked decrease in resistance and a clearly audible "click".

5. A method according to claim 4, in which the end face of said mandrin is ground at an angle of at least 40° to the axis of the mandrin.

6. A method according to claim 4, in which the area of said end face of said mandrin is reduced by grinding tapered facets on opposite sides of the outermost part of the tip portion of the mandrin, said facets being ground symmetrical to one another with respect to an axial plane perpendicular to the end face of the mandrin and reducing the area of said end face cutting into the bore of said mandrin.

* * * * *